United States Patent [19]

Bai et al.

[11] 4,147,592

[45] Apr. 3, 1979

[54] PURIFICATION OF UROKINASE

[75] Inventors: Yasuo Bai, Sakai; Hideki Yanagi, Toyonaka; Junichi Yoshikawa; Shigeo Ogino, both of Nishinomiya, all of Japan

[73] Assignee: Sumitomo Chemical Company Limited, Osaka, Japan

[21] Appl. No.: 883,746

[22] Filed: Mar. 6, 1978

[30] Foreign Application Priority Data

Mar. 10, 1977 [JP] Japan .................................. 52/26726

[51] Int. Cl.² ........................................... C07G 7/026
[52] U.S. Cl. .................................... 195/66 B; 195/62; 210/24
[58] Field of Search ................. 195/66 B, 62; 210/24, 210/31 R, 31 C, 36, 37 R, 40; 424/94, 99

[56] References Cited

U.S. PATENT DOCUMENTS

| | | | |
|---|---|---|---|
| 2,983,647 | 5/1961 | Kjeldgaard et al. ..................... | 167/73 |
| 3,256,158 | 6/1966 | White ................................. | 195/66 B |
| 3,256,158 | 6/1966 | White ................................. | 195/66 B |
| 3,723,252 | 3/1973 | Ogawa et al. ......................... | 195/66 B |
| 3,957,582 | 5/1976 | Stried et al. ........................ | 195/66 B |
| 4,010,074 | 3/1977 | Vemura et al. ........................ | 195/66 B |
| 4,066,506 | 1/1978 | Johnson et al. ....................... | 195/66 B |

FOREIGN PATENT DOCUMENTS

2627125 12/1976 Fed. Rep. of Germany.
51-67787 6/1976 Japan.

OTHER PUBLICATIONS

Sgouris et al., "The Purification, Assay, Sterilization, and Removal of Pyrogenicity of Human Urokinase", in *Vox Sanguinis*, vol. 7, pp. 739–749 (1962).

*Primary Examiner*—Charles N. Hart
*Assistant Examiner*—Ivars Cintins
*Attorney, Agent, or Firm*—Stevens, Davis, Miller & Mosher

[57] ABSTRACT

A process for purifying urokinase which comprises contacting a crude aqueous solution of urokinase with an ionic pullulan gel and thereafter separating and recovering an aqueous solution of urokinase devoid of harmful impurities.

3 Claims, No Drawings

PURIFICATION OF UROKINASE

The present invention relates to a method for purifying urokinase. More particularly, the invention pertains to a process for removing harmful impurities from crude urokinase preparations, which comprises contacting an aqueous solution of crude urokinase with an ionic pullulan gel and thereafter separating and recovering urokinase in a highly purified aqueous solution form.

It is known that urokinase has been used for the treatment of thrombosis, and particularly in recent years, it is used for the treatment of tumors in combination with anti-tumor agents in order to enhance the effectiveness of anti-tumor agents.

It is also known that urokinase can be recovered from human urine by various methods.

For example, it can be obtained by contacting urine with adsorbing agents, eluating the adsorbates, and recovering the fractions having urokinase activity.

However, urokinase obtained by such methods is not sufficiently pure for its therapeutical use. It therefore can not be used for the preparation of injections without further purification. Particularly, pyrogens and coloring matter have to be removed therefrom.

It has now been found that the purification of crude urokinase can effectively and advantageously be carried out by the use of an ionic pullulan gel. In the present invention, harmful impurities such as pyrogens and coloring matter are sufficiently eliminated from crude urokinase by contacting crude urokinase with an ionic pullulan gel in an aqueous solution and then recovering fractions having urokinase activity therefrom.

The ionic pullulan gel used in the invention can be prepared by reacting a hydrophilic pullulan gel with a compound of the formula,

 (I)

or a compound of the formula,

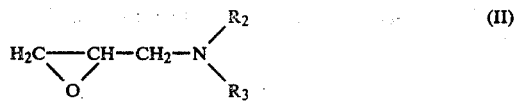 (II)

wherein Hal is halogen, $R_1$ is alkylene having 1 to 5 carbon atoms, and $R_2$ and $R_3$ are each hydrogen, a lower alkyl, phenyl or lower alkyl-substituted phenyl group, in the presence of an alkali and a suitable solvent.

Suitable examples of the amino compounds of formula (I) are 2-dimethylaminoethyl chloride, 2-diethylaminoethyl chloride, 2-dimethylaminoisopropyl chloride, 2-bromo-5-diethylaminopentane, 2-diphenylaminoethyl chloride, 3-(N,N-dimethylphenylamino)ethyl chloride and the like.

Suitable examples of the amino compounds of the formula (II) are 3-amino-1,2-epoxypropane, 3-dimethylamino-1,2-epoxypropane, 3-diethylamino-1,2-epoxypropane, 3-dibutylamino-1,2-epoxypropane, 3-diphenylamino-1,2-epoxypropane, 3-(N,N-dimethylphenylamino)-1,2-epoxypropane, N,N-(2,3-epoxypropyl)methylaniline, and the like.

The amino compounds (I) and (II) may also be used in the form of salts (e.g salts with chloroacetic acid, bromoacetic acid, chloropropionic acid, chloromethanesulfonic acid, bromoethanesulfonic acid, chloroethanesulfonic acid, etc.).

The amino compounds (I) and (II) are used in an amount in excess of the stoichiometric amount in order to promote the reaction. It is desirable to use 1/30 to 10 moles, preferably 0.1 to 5 moles of the above compounds per mole of the glucose unit in pullulan.

The alkaline substances used in reacting the hydrophilic pullulan gel with the above-noted compound include alkali metal hydroxides such as sodium hydroxide and potassium hydroxide, alkali earth metal hydroxides such as calcium hydroxide and magnesium hydroxide, and, in some cases, organic amines such as ethylenediamine, diethylenetriamine and triethylamine. Of these compounds sodium hydroxide is most preferred. The amount to be added of the alkaline substance is generally 0.1 to 10 times as much as the molar amount of the aforementioned compound to be reacted with the hydrophilic pullulan gel. However, in the case where a hydrogen halide is liberated during the reaction, it is necessary to use the alkaline substance in an amount sufficient for neutralization.

As for the reaction solvent, there is no special limitation so long as it does not adversely affect the reaction. Suitable solvents are water, dimethyl sulfoxide, N,N-dimethylformamide, N,N-dimethylacetamide, benzene, toluene, chloroform, and ethyl acetate. Of these solvents, water is preferred.

The reaction conditions are also not particularly restricted. Although a reaction temperature below 200° C. is generally suitable, undesirable side reactions would take place in some cases at a temperature exceeding 100° C. Therefore, a reaction temperature of 10° C. to 100° C. is more desirable.

Instead of the amino compounds (I) and (II), alkyleneimines such as ethyleneimine and propyleneimine can be used for the preparation of the ionic pullulan gel.

The hydrophilic pullulan gel used in the preparation of the ionic pullulan gel is obtained, as already disclosed in German Patent Application Laid-Open (DT-OS) No. 2,627,125, by crosslinking pullulan with a bifunctional compound represented by the formula

 (III)

wherein X and Z are each a halogen atom or an epoxy group and Y is an aliphatic residue having 1 to 30, preferably 1 to 6 carbon atoms.

The crosslinking reaction for producing the hydrophilic gel can preferably carried out in water or a mixture of water and acetone or water and alcohol in the presence of an alkali (e.g. sodium hydroxide, potassium hydroxide, calcium hydroxide, etc.) at a temperature from 10° C. to 70° C. for 1 to 24 hours, preferably 2 to 10 hours.

Examples of suitable bifunctional compounds include epichlorohydrin, epibromohydrin, dichlorohydrin, dibromohydrin, ethylene glycol diglycidyl ether, triethylene glycol diglycidyl ether, diglycidyl ether, and 1,6-hexanediol diglycidyl ether.

The ionic pullulan gel of the present invention can also be prepared by reacting pullulan with said amino compound (I) or (II) in a suitable solvent in the presence of an alkali and then crosslinking the resulted pullulan aminoalkyl ether with said bifunctional compound (III) in the presence of an alkali in an aqueous solvent.

The preparation of the pullulan aminoalkyl ether can be carried out as follows:

The amount of the amines to be reacted with pullulan is 0.001 to 10, preferably 0.01 to 10 moles per glucose unit of pullulan, depending on the amine content of the intended pullulan aminoalkyl ether.

The reaction can be carried in a suitable solvent.

The solvent to be used in the reaction is not limited to any type, but a solvent which dissolves one or both of the pullulan and the aminoalkylating agent is preferred. For example, water, dimethyl sulfoxide, dimethylformaldehyde, and dimethylacetamide are used.

The reaction can be preferably conducted at a temperature from 0° C. to 200° C.

The crosslinking of the pullulan aminoalkyl can be conducted by using the pullulan aminoalkyl ether of which number ratio of hydroxy group to amino group is 0.001 to 2.0 with substantially the same procedures as in crosslinking the hydrophilic pullulan gel with the bifunctional compound (III).

The purification process of the present invention can be carried out by contacting crude urokinase with an ionic pullulan gel in a buffer solution having a pH range between 6.0 and 9.0, preferably between 7.0 and 8.0, and an electrolyte concentration ranging from 0.01 molar to 0.10 molar, preferably 0.05 molar, so that the ionic pullulan gel may adsorb the impurities contained in the crude urokinase, and separating and recovering the solution having urokinase activity.

The contacting of crude urokinase with an ionic pullulan gel can be carried out by using column chromatographic technique or batchwise operation in a conventional way.

For example, it can be accomplished by adding an ionic pullulan gel previously swollen with a buffer solution to crude urokinase dissolved in a buffer solution and, if necessary, stirring the mixture, or it can be carried out by passing crude urokinase buffer solution through a column of an ionic pullulan gel.

In the present invention, an ionic pullulan gel is generally used in an amount of from 5.0 to 300 g, preferably 60 to 160 g in dry state, per liter of crude urokinase buffer solution which contains crude urokinase having at least 5,000 units per mg of total protein, preferably at least 10,000 units per mg of total protein, in an amount ranging from $5 \times 10^5$ to $1 \times 10^8$ units, preferably from $1 \times 10^7$ to $5 \times 10^7$ units. The urokinase activity is determined according to the fibrin plate method disclosed in Ploug, J. Biochim. Biophys. Acta. No. 24, p 278 (1954).

Examples of buffers used in the present invention are phosphate, trishydroxyaminomethane and borate buffers.

The contacting of the present invention is usually carried out at a temperature of from 0° C. to 100° C., preferably 4° C. to 30° C., but the contacting temperature is not particularly limited thereto.

For the purpose of the present invention, it is particularly preferable to employ an ionic pullulan gel which has a water-regain ranging from 1.0 to 20 g, preferably 2 to 5 g, per g of dry gel and an ion exchange capacity in a range from 1 to 4, preferably 2.0 to 3.0 meq/g, and of which particle size is in a range from 30 to 200μ, preferably from 40 to 120μ.

Among the ionic pullulan gels, the one which has diethylaminoethyl groups in its molecule is particularly effective for purifying urokinase.

The urokinase solution obtained as above contains no harmful impurities and urokinase sufficiently pure for its parenteral use can be isolated therefrom by a conventional method.

The following examples are given to illustrate the present invention more precisely but they should not be construed to limit the present invention thereto. In the following examples, the pyrogen tests were carried out according to pharmacopeia of Japan, 9th edition. Urokinase activity was determined by aforesaid method. Unless otherwise indicated, all parts are by weight in the reference example.

REFERENCE EXAMPLE

Preparation of an ionic pullulan gel:

40 parts of pullulan (average molecular weight 67000) was dissolved in 70 parts of water and admixed with 20 parts of 15.6 N aqueous sodium hydroxide solution to form a uniform aqueous solution. This aqueous solution was added slowly to a dispersion medium containing 14 parts of polyvinyl acetate and 300 parts of toluene, while mechanical stirring at 600 rpm was continued to disperse said aqueous solution in the form of droplets. One hour after the addition of the aqueous solution, 24.5 parts of epichlorohydrin was added to the dispersion and allowed to react at 50° C. for 5 hours. Thereafter, the precipitated gel was collected and washed with toluene, methanol and a dilute aqueous solution of hydrochloric acid, successively. The gel was dispersed in water, shrunk with ethanol, filtered and dried at 70° C. for 24 hours in vacuo to obtain 41 parts of pullulan gel (water-regain 2.5 g/g of dry gel) in spherical bead form.

16.2 parts of the pullulan gel obtained as above was dispersed in a solution of 46 parts of sodium hydroxide in 150 parts of water, and a solution of 86 parts of 2-diethylaminoethyl chloride hydrochloride in 100 parts of water was dropwisely added thereto in 4 hours, while the dispersion was stirred at room temperature. After additional 16 hour stirring at room temperature, the mixture was adjusted to pH 3 with hydrochloric acid. The product was washed with water and methanol to give diethylaminoethylated pullulan gel (DEAE-pullulan gel) in spherical bead form (water-regain: 3.9 g/g of dry gel, amine content: 3.1 meq/g, when measured by conductomeric titration, ion exchange capacity: 3.1 meq/g).

EXAMPLE 1

DEAE-pullulan gel (water-regain: 3.8 g/g of dry gel, ion exchange capacity: 3.1 meq/g) was swollen with 0.025 M, pH 8.0 phosphate buffer ($Na_2HPO_4$, $NaH_2PO_4$) solution containing sodium chloride in 0.025 molar concentration and packed into a column (0.6 cm in diameter, gel bed volume 0.706 cm$^3$).

By dissolving crude urokinase into 5.5 ml of the same buffer solution as used above, there was obtained a colored crude urokinase solution containing 6000 units of urokinase (purity: 8,040 units per mg of total protein).

This crude urokinase solution was passed through the column to give 7.0 ml of a colorless buffer solution containing 5,800 units of urokinase (purity: 26,300 units per mg of total protein), in which solution no pyrogen was found.

EXAMPLE 2

One gram of DEAE-pullulan gel (water regain: 3.8 g/g of dry gel, ion exchange capacity: 3.1 meq/g) was treated with a 0.025 M, pH 7.4 phosphate buffer ($Na_2HPO_4$, $NaH_2PO_4$) solution containing sodium chloride in 0.025 molar concentration and centrifuged at 3,000 rpm for 15 minutes to give swollen DEAE-pullulan gel.

By dissolving colored crude urokinase into 10 ml of the same buffer solution as above, there was obtained a colored crude urokinase solution containing 30,000 units of urokinase (purity: 8,040 units per mg of total protein). The swollen DEAE-pullulan gel was added to the crude urokinase solution and stirred for 30 minutes. The mixture was centrifuged at 3,000 rpm for 15 minutes to give 10 ml of colorless solution containing 24,700 units of urokinase (purity: 28,900 units per mg of total protein). In this solution, no pyrogen was found.

EXAMPLE 3

DEAE-pullulan gel (ion exchange capacity: 2.3 meq/g, water-regain: 3.6 g/g of dry gel) was swollen with 0.025 M, pH 8.0 phosphate buffer ($Na_2HPO_4$, $NaH_2PO_4$) solution and packed into a column (1.5 cm in diameter, gel bed volume 7.0 cm³). By dissolving crude urokinase into 11.6 ml of the same buffer solution as above, there was obtained a crude urokinase solution containing 250,000 units of urokinase (purity: 29,000 units per mg of total protein). This crude urokinase solution was passed through the column to give 16.5 ml of a colorless solution containing 235,000 units of urokinase (purity: 88,000 units per mg of total protein). No pyrogen was found in this solution.

EXAMPLE 4

One gram of DEAE-pullulan gel (ion exchange capacity: 2.3 meq/g, water-regain: 3.6 g/g of dry gel) was treated with a 0.025 M, pH 8.0 phosphate buffer ($Na_2HPO_4$, $NaH_2PO_4$) and centrifuged at 3,000 rpm for 10 minutes to give swollen DEAE-pullulan gel.

By dissolving crude urokinase into 10 ml of the same buffer solution as above, there was obtained a colored crude urokinase solution containing 214,000 units of urokinase (purity: 29,000 units per mg of total protein).

This crude urokinase solution was added to the swollen DEAE-pullulan gel and stirred for 20 minutes. The mixture was centrifuged at 3000 rpm for 15 minutes to give 10 ml of a colorless solution containing 182,000 units of urokinase (purity: 82,000 units per mg of total protein). No pyrogen was found in this solution.

What is claimed is:

1. A process for purifying urokinase which comprises contacting a crude aqueous solution of urokinase with an ionic pullulan gel within a pH range from 6.0 to 9.0 and thereafter separating and recovering therefrom a pure urokinase solution.

2. A process according to claim 1, wherein the contacting is carried out by using an ionic pullulan gel having a water-regain ranging from 1.0 to 20 g per g of dry gel and an ion exchange capacity ranging from 1 to 4 meq/g.

3. A process according to claim 2, wherein the ionic pullulan gel has diethylaminoethyl groups as ion exchangers.

* * * * *